US012583925B2

(12) United States Patent
Li et al.

(10) Patent No.: US 12,583,925 B2
(45) Date of Patent: Mar. 24, 2026

(54) BISPECIFIC ANTIBODIES TARGETING PD1 AND VEGF

(71) Applicant: LANOVA MEDICINES LIMITED, Shanghai (CN)

(72) Inventors: Runsheng Li, Shanghai (CN); Wei Cao, Shanghai (CN); Haijuan Gu, Shanghai (CN); Wentao Huang, Shanghai (CN); Ying Qin Zang, Shanghai (CN)

(73) Assignee: LANOVA MEDICINES LIMITED, Shanghai (CN)

( * ) Notice: Subject to any disclaimer, the term of this patent is extended or adjusted under 35 U.S.C. 154(b) by 0 days.

(21) Appl. No.: 18/897,951

(22) Filed: Sep. 26, 2024

(65) Prior Publication Data

US 2025/0019442 A1      Jan. 16, 2025

Related U.S. Application Data

(63) Continuation of application No. PCT/CN2023/137517, filed on Dec. 8, 2023.

(30) Foreign Application Priority Data

Dec. 12, 2022    (WO) ............... PCT/CN2022/138363

(51) Int. Cl.
| | |
|---|---|
| *C07K 16/00* | (2006.01) |
| *A61K 39/00* | (2006.01) |
| *A61P 35/00* | (2006.01) |
| *C07K 16/22* | (2006.01) |
| *C07K 16/28* | (2006.01) |

(52) U.S. Cl.
CPC .......... *C07K 16/2818* (2013.01); *A61P 35/00* (2018.01); *C07K 16/22* (2013.01); *A61K 2039/505* (2013.01); *C07K 2317/31* (2013.01); *C07K 2317/33* (2013.01); *C07K 2317/52* (2013.01); *C07K 2317/55* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,892,019 A | 4/1999 | Schlom et al. | |
| 6,150,584 A | 11/2000 | Kucherlapati et al. | |
| 6,420,140 B1 | 7/2002 | Hori et al. | |
| 6,458,592 B1 | 10/2002 | Jakobovits et al. | |
| 11,827,697 B2 | 11/2023 | Yang et al. | |
| 2020/0347135 A1 | 11/2020 | Zhang et al. | |
| 2022/0204626 A1 | 6/2022 | Fang | |
| 2022/0259330 A1 | 8/2022 | Zhao et al. | |
| 2022/0281997 A1 | 9/2022 | Qin et al. | |
| 2022/0332824 A1* | 10/2022 | Yin .................. | C07K 16/2818 |
| 2023/0027029 A1* | 1/2023 | Zhang ............... | C07K 16/2818 |
| 2023/0322953 A1 | 10/2023 | He et al. | |

FOREIGN PATENT DOCUMENTS

| | | | |
|---|---|---|---|
| AU | 2023387779 A1 | 8/2024 | |
| AU | 2023287932 A1 | 12/2024 | |
| AU | 2023310484 A1 | 2/2025 | |
| CN | 111699200 A | 9/2020 | |
| CN | 113214400 A | 8/2021 | |
| CN | 115558029 A | 1/2023 | |
| TW | I802633 B | 5/2023 | |
| TW | I806088 B | 6/2023 | |
| WO | WO 2019154349 A1 | 8/2019 | |
| WO | WO 2021004480 A1 | 1/2021 | |
| WO | WO 2021057978 A1 | 4/2021 | |
| WO | WO 2021119832 A1 | 6/2021 | |
| WO | WO 2021185337 A1 | 9/2021 | |
| WO | WO 2021218684 A1 | 11/2021 | |
| WO | WO 2022143801 A1 | 7/2022 | |
| WO | WO 2023134787 A2 | 7/2023 | |
| WO | WO 2023134787 A3 | 7/2023 | |
| WO | WO 2023147371 A1 | 8/2023 | |
| WO | WO 2023169559 A1 | 9/2023 | |
| WO | WO 2023196784 A1 | 10/2023 | |
| WO | WO 2023246247 A1 | 12/2023 | |
| WO | WO 2024017281 A1 | 1/2024 | |
| WO | WO 2024120199 A1 | 6/2024 | |
| WO | WO 2024141027 A1 | 7/2024 | |

OTHER PUBLICATIONS

International Search Report for PCT/CN2023/137517, mailed Jan. 26, 2024, 4 pages.
Written Opinion of the International Searching Authority for PCT/CN2023/137517, mailed Jan. 26, 2024, 3 pages.
Wu et al., 1987, "Receptor-mediated in vitro gene transformation by a soluble DNA carrier system," J. Biol. Chem., 262(10):4429-4432.

* cited by examiner

*Primary Examiner* — Joanne Hama
*Assistant Examiner* — Estella M. Gustilo
(74) *Attorney, Agent, or Firm* — JONES DAY

(57) ABSTRACT

Provided are bispecific antibodies capable of binding to human VEGF protein and human PD-1 protein. These bispecific antibodies are effective in treating cancer.

60 Claims, 10 Drawing Sheets

Specification includes a Sequence Listing.

SEQUENCE LISTING

```
Sequence total quantity: 19
SEQ ID NO: 1            moltype = AA  length = 123
FEATURE                 Location/Qualifiers
source                  1..123
                        mol_type = protein
                        organism = synthetic construct
SEQUENCE: 1
EVQLVESGGG LVQPGGSLRL SCAVSGNIYN RNFMGWFRQA PGKGREGVSA IYTGTSRTYY  60
ADSVKGRFTI SRDNAKNTVY LQMNSLRPED TAVYYCAADL RDGFWDTGVW NTWGQGTLVT  120
VSS                                                                123

SEQ ID NO: 2            moltype = AA  length = 123
```

```
FEATURE                 Location/Qualifiers
source                  1..123
                        mol_type = protein
                        organism = synthetic construct
SEQUENCE: 2
EVQLVESGGG LVQPGGSLRL SCAVSGNIYN RNFMGWFRQA PGKGLEGVSA IYTGTSRTYY   60
ADSVKGRFTI SRDNSKNTVY LQMNSLRAED TAVYYCAADL REGFWDTGVW NTWGQGTLVT  120
VSS                                                               123

SEQ ID NO: 3            moltype = AA   length = 123
FEATURE                 Location/Qualifiers
source                  1..123
                        mol_type = protein
                        organism = synthetic construct
SEQUENCE: 3
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSS                                                               123

SEQ ID NO: 4            moltype = AA   length = 107
FEATURE                 Location/Qualifiers
source                  1..107
                        mol_type = protein
                        organism = synthetic construct
SEQUENCE: 4
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIK                107

SEQ ID NO: 5            moltype = AA   length = 5
FEATURE                 Location/Qualifiers
source                  1..5
                        mol_type = protein
                        organism = synthetic construct
SEQUENCE: 5
RNFMG                                                               5

SEQ ID NO: 6            moltype = AA   length = 17
FEATURE                 Location/Qualifiers
source                  1..17
                        mol_type = protein
                        organism = synthetic construct
SEQUENCE: 6
AIYTGTSRTY YADSVKG                                                 17

SEQ ID NO: 7            moltype = AA   length = 14
FEATURE                 Location/Qualifiers
source                  1..14
                        mol_type = protein
                        organism = synthetic construct
SEQUENCE: 7
DLRDGFWDTG VWNT                                                    14

SEQ ID NO: 8            moltype = AA   length = 14
FEATURE                 Location/Qualifiers
source                  1..14
                        mol_type = protein
                        organism = synthetic construct
SEQUENCE: 8
DLREGFWDTG VWNT                                                    14

SEQ ID NO: 9            moltype = AA   length = 5
FEATURE                 Location/Qualifiers
source                  1..5
                        mol_type = protein
                        organism = synthetic construct
SEQUENCE: 9
NYGMN                                                               5

SEQ ID NO: 10           moltype = AA   length = 17
FEATURE                 Location/Qualifiers
source                  1..17
                        mol_type = protein
                        organism = synthetic construct
SEQUENCE: 10
WINTYTGEPT YAADFKR                                                 17

SEQ ID NO: 11           moltype = AA   length = 14
FEATURE                 Location/Qualifiers
source                  1..14
```

21

22

-continued

```
                              mol_type = protein
                              organism = synthetic construct
SEQUENCE: 11
YPHYYGSSHW YFDV                                                        14

SEQ ID NO: 12       moltype = AA   length = 11
FEATURE             Location/Qualifiers
source              1..11
                    mol_type = protein
                    organism = synthetic construct
SEQUENCE: 12
SASQDISNYL N                                                           11

SEQ ID NO: 13       moltype = AA   length = 7
FEATURE             Location/Qualifiers
source              1..7
                    mol_type = protein
                    organism = synthetic construct
SEQUENCE: 13
FTSSLHS                                                                7

SEQ ID NO: 14       moltype = AA   length = 9
FEATURE             Location/Qualifiers
source              1..9
                    mol_type = protein
                    organism = synthetic construct
SEQUENCE: 14
QQYSTVPWT                                                              9

SEQ ID NO: 15       moltype = AA   length = 20
FEATURE             Location/Qualifiers
source              1..20
                    mol_type = protein
                    organism = synthetic construct
SEQUENCE: 15
GGGGSGGGGS GGGGSGGGGS                                                  20

SEQ ID NO: 16       moltype = AA   length = 739
FEATURE             Location/Qualifiers
source              1..739
                    mol_type = protein
                    organism = synthetic construct
SEQUENCE: 16
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT      120
VSSASTKGPS VFPLAPSSKS TSGGTAALGC LVKDYFPEPV TVSWNSGALT SGVHTFPAVL      180
QSSGLYSLSS VVTVPSSSLG TQTYICNVNH KPSNTKDKK VEPKSCDKTH TCPPCPAPEA       240
AGGPSVFLFP PKPKDTLMIS RTPEVTCVVV DVSHEDPEVK FNWYVDGVEV HNAKTKPREE      300
QYNSTYRVVS VLTVLHQDWL NGKEYKCKVS NKALPAPIEK TISKAKGQPR EPQVYTLPPS      360
RDELTKNQVS LTCLVKGFYP SDIAVEWESN GQPENNYKTT PPVLDSDGSF FLYSKLTVDK      420
SRWQQGNVFS CSVMHEALHN HYTQKSLSLS PGKGGGGSGG GGSGGGGSGG GGSEVQLVES      480
GGGLVQPGGS LRLSCAVSGN IYNRNFMGWF RQAPGKGREG VSAIYTGTSR TYYADSVKGR      540
FTISRDNAKN TVYLQMNSLR PEDTAVYYCA ADLRDGFWDT GVWNTWGQGT LVTVSSGGGG      600
SGGGGSGGGG SGGGGSEVQL VESGGGLVQP GGSLRLSCAV SGNIYNRNFM GWFRQAPGKG      660
REGVSAIYTG TSRTYYADSV KGRFTISRDN AKNTVYLQMN SLRPEDTAVY YCAADLRDGF      720
WDTGVWNTWG QGTLVTVSS                                                   739

SEQ ID NO: 17       moltype = AA   length = 214
FEATURE             Location/Qualifiers
source              1..214
                    mol_type = protein
                    organism = synthetic construct
SEQUENCE: 17
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 18       moltype = AA   length = 595
FEATURE             Location/Qualifiers
source              1..595
                    mol_type = protein
                    organism = synthetic construct
SEQUENCE: 18
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT      120
VSSASTKGPS VFPLAPSSKS TSGGTAALGC LVKDYFPEPV TVSWNSGALT SGVHTFPAVL      180
QSSGLYSLSS VVTVPSSSLG TQTYICNVNH KPSNTKVDKK VEPKSCDKTH TCPPCPAPEA      240
AGGPSVFLFP PKPKDTLMIS RTPEVTCVVV DVSHEDPEVK FNWYVDGVEV HNAKTKPREE      300
```

-continued

```
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGGGGGSGGG GSGGGGSGGG GSEVQLVESG 480
GGLVQPGGSL RLSCAVSGNI YNRNFMGWFR QAPGKGREGV SAIYTGTSRT YYADSVKGRF 540
TISRDNAKNT VYLQMNSLRP EDTAVYYCAA DLRDGFWDTG VWNTWGQGTL VTVSS      595

SEQ ID NO: 19          moltype = AA  length = 595
FEATURE                Location/Qualifiers
source                 1..595
                       mol_type = protein
                       organism = synthetic construct
SEQUENCE: 19
EVQLVESGGG LVQPGGSLRL SCAASGYTFT NYGMNWVRQA PGKGLEWVGW INTYTGEPTY 60
AADFKRRFTF SLDTSKSTAY LQMNSLRAED TAVYYCAKYP HYYGSSHWYF DVWGQGTLVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGGGGGSGGG GSGGGGSGGG GSEVQLVESG 480
GGLVQPGGSL RLSCAVSGNI YNRNFMGWFR QAPGKGLEGV SAIYTGTSRT YYADSVKGRF 540
TISRDNSKNT VYLQMNSLRA EDTAVYYCAA DLREGFWDTG VWNTWGQGTL VTVSS      595
```

BISPECIFIC ANTIBODIES TARGETING PD1 AND VEGF

CROSS REFERENCE TO RELATED APPLICATIONS

The present application is a continuation of International Application No. PCT/CN2023/137517, filed Dec. 8, 2023, which claims priority to International Application No. PCT/CN2022/138363, filed Dec. 12, 2022, the content of each of which is incorporated herein by reference in its entirety in the present disclosure.

REFERENCE TO AN ELECTRONIC SEQUENCE LISTING

The contents of the electronic sequence listing (70LG-366210-US.xml; Size: 20,042 bytes; and Date of Creation: Sep. 26, 2024) is herein incorporated by reference in its entirety.

BACKGROUND

Vascular endothelial growth factor (VEGF) stimulates the formation of blood vessels. VEGF is involved in both vasculogenesis and angiogenesis. VEGF's normal function is to create new blood vessels during embryonic development, new blood vessels after injury, muscle following exercise, and new vessels to bypass blocked vessels.

VEGF can contribute to disease development too. Solid cancers cannot grow beyond a limited size without an adequate blood supply. Cancers that can express VEGF are able to grow and metastasize. Also, overexpression of VEGF can cause vascular disease in the retina of the eye and other parts of the body. Inhibition of VEGF can be useful for the treatment of certain cancers and in age-related macular degeneration.

Programmed cell death protein 1, also known as PD-1 and CD279 (cluster of differentiation 279), is a protein on the surface of T and B cells that has a role in regulating the immune system's response to the cells of the human body by down-regulating the immune system and promoting self-tolerance by suppressing T cell inflammatory activity. This prevents autoimmune diseases, but it can also prevent the immune system from killing cancer cells.

PD-1 is an immune checkpoint and guards against auto-immunity through two mechanisms. First, it promotes apoptosis (programmed cell death) of antigen-specific T-cells in lymph nodes. Second, it reduces apoptosis in regulatory T cells (anti-inflammatory, suppressive T cells).

PD-L1, the ligand for PD1, is highly expressed in several cancers and hence the role of PD1 in cancer immune evasion is well established. Monoclonal antibodies targeting PD-1 that boost the immune system are being developed for the treatment of cancer. Inhibition of the interaction between PD-1 and PD-L1 can enhance T-cell responses and mediate antitumor activity.

Bispecific antibodies targeting both the VEGF and PD-1 proteins have been proposed, but development of bispecific antibodies with good stability and activity has been proved to be challenging.

SUMMARY

The present disclosure provides bispecific antibodies having binding specificities to both VEGF and PD-1 proteins. As shown in the experimental examples, these bispecific antibodies exhibited high binding affinity to both proteins and were effective in inhibiting VEGF enzymatic activities and blocking PD-1 to PD-L1 binding, resulting in T-cell activation.

One embodiment of the present disclosure provides a bispecific antibody comprising an anti-VEGF portion and an anti-PD-1 portion, wherein the anti-VEGF portion comprises an anti-VEGF antibody or antigen binding fragment having binding specificity to a human VEGF protein, which comprises a heavy chain variable region (VH) comprising a CDRH1 comprising the amino acid sequence of SEQ ID NO:9, a CDRH2 comprising the amino acid sequence of SEQ ID NO:10, and a CDRH3 comprising the amino acid sequence of SEQ ID NO: 11, and a light chain variable region (VL) comprising a CDRL1 comprising the amino acid sequence of SEQ ID NO:12, a CDRL2 comprising the amino acid sequence of SEQ ID NO: 13, and a CDRL3 comprising the amino acid sequence of SEQ ID NO: 14, and wherein the anti-PD-1 portion comprises an anti-PD-1 single domain antibody having binding specificity to a human PD-1 protein, which comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7 or 8.

In some embodiments, In some embodiments, the VH of the anti-VEGF antibody or antigen binding fragment comprises the amino acid sequence of SEQ ID NO:3, and the VL of the anti-VEGF antibody or antigen binding fragment comprises the amino acid sequence of SEQ ID NO:4.

In some embodiments, the anti-VEGF antibody or antigen binding fragment is a full size Fab antibody. In some embodiments, the full size Fab antibody comprises an IgG Fc fragment. In some embodiments, the IgG Fc fragment comprises LALA mutations.

In some embodiments, the anti-PD-1 single domain antibody comprises the amino acid sequence of SEQ ID NO:1 or 2.

In some embodiments, the anti-PD-1 single domain antibody is deposited at the C-terminal side of the anti-VEGF antibody or antigen binding fragment thereof. In some embodiments, the anti-PD-1 single domain antibody is fused, through a (G4S) 4 (SEQ ID NO: 15) linker, to the C-terminus of the anti-VEGF antibody. In some embodiments, the bispecific antibody comprises a single anti-PD-1 single domain antibody on each peptide chain of the bispecific antibody. In some embodiments, the bispecific antibody comprises two anti-PD-1 single domain antibodies on each peptide chain of the bispecific antibody. In some embodiments, the two anti-PD-1 single domain antibodies on each peptide chain is linked through a (G4S) 4 (SEQ ID NO:15) linker.

In one embodiment, provided is a bispecific antibody that comprises the amino acid sequences of SEQ ID NO:16 and 17. In one embodiment, provided is a bispecific antibody that comprises the amino acid sequences of SEQ ID NO:18 and 17. In one embodiment, provided is a bispecific antibody that comprises the amino acid sequences of SEQ ID NO:19 and 17.

Also provided, in one embodiment, is a composition comprising the bispecific antibody of the present disclosure and a pharmaceutically acceptable carrier. Further provided is one or more polynucleotide encoding a heavy chain of the bispecific antibody of the present disclosure. In one embodiment, the one or more polynucleotide encodes the bispecific antibody.

Yet another embodiment provides a cell comprising the one or more polynucleotide of the present disclosure. Another embodiment provides a method of treating cancer in a patient in need thereof, comprising administering to the patient the bispecific antibody. In some embodiments, the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

DETAILED DESCRIPTION

Definitions

Figure 1:
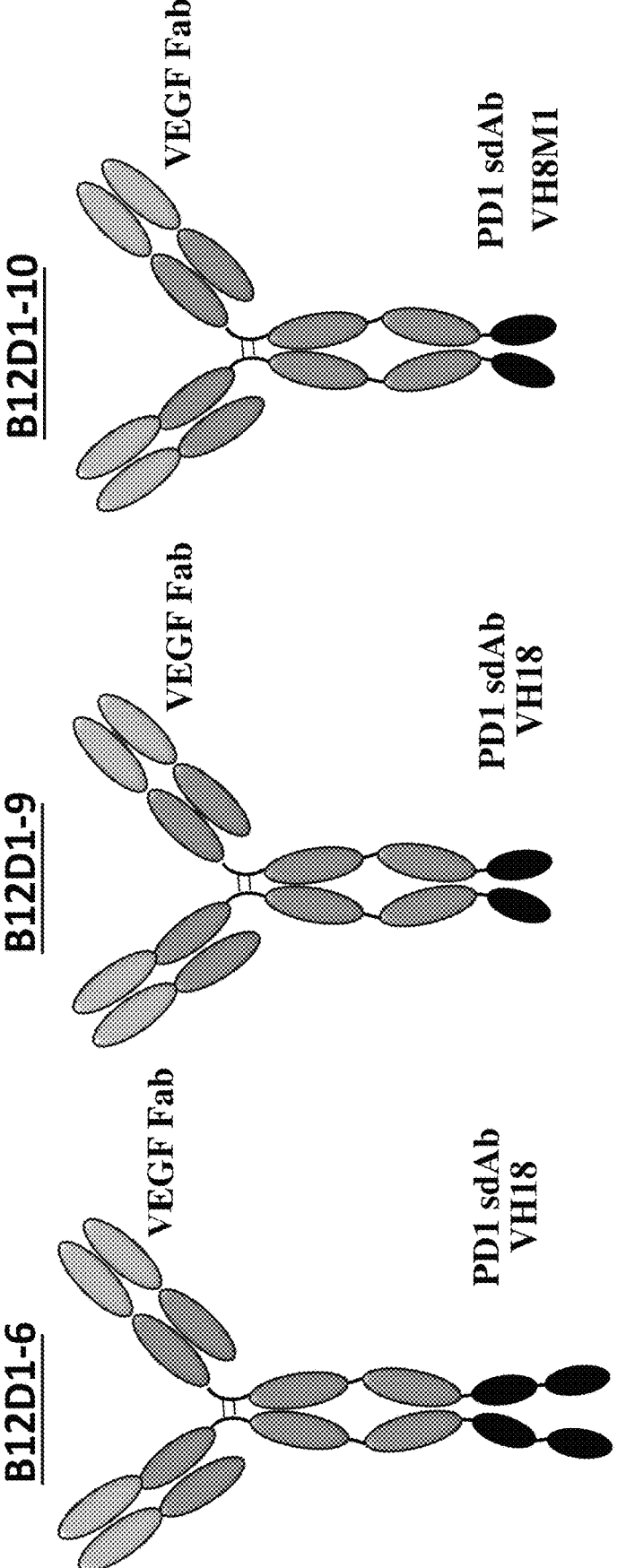
FIG. 1 shows the schematic of anti-PD1-VEGF bispecific antibodies.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. ScFv molecules are known in the art and are described, e.g., in U.S. Pat. No. 5,892,019.

A "single domain antibody" (sdAb or VHH), also known as a nanobody, is an antibody fragment consisting of a single monomeric variable antibody domain. Like a whole antibody, it is able to bind selectively to a specific antigen. With a molecular weight of only 12-15 kDa, single domain antibodies are much smaller than common antibodies (150-160 kDa).

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Anti-VEGF Anti-PD-1 Bispecific Antibodies

The present disclosure provides anti-VEGF anti-PD-1 bispecific antibodies with high affinity and inhibitory activity to both human VEGF and PD-1 proteins. The antibodies can bind effectively to both soluble and cell surfaces VEGF and PD-1, at comparable levels to their parental antibodies and to benchmark anti-VEGF anti-PD-1 bispecific antibody VP101 developed by Akeso. Surprisingly, however, one of the tested bispecific antibodies, B12D1-6, significantly outperformed VP101 (Example 5 and FIG. 7A-B).

The structures of the bispecific antibodies are illustrated in FIG. 1. In all bispecific antibodies, one (B12D1-9 and B12D1-10) or two (B12D1-6) anti-PD-1 nanobody/VHH (VH18 or VH8M1) were fused to the C-terminus of a full size, LALA-mutated, IgG1 antibody of Bevacizumab. Therefore, B12D1-6 contained 4 anti-PD-1 VHH and each of B12D1-9 and B12D1-10 contained only 2 anti-PD-1 VHH.

In accordance with one embodiment of the present disclosure, provided is a bispecific antibody that has binding specificities to both human VEGF and PD-1 protein. In some embodiments, the bispecific antibody includes an anti-VEGF portion (or anti-VEGF unit) and an anti-PD-1 portion (or anti-PD-1 unit). The term "portion" or "unit" as used herein refers to part of a bispecific antibody, which typically includes one or two fragments, having the desired binding activity. Each portion includes one or more antibody or antigen binding fragment.

In one embodiment, the bispecific antibody has an anti-VEGF portion, which preferably includes a Fab fragment (two VH/VL pairs), or further with a Fc fragment to form a full-sized IgG antibody. In some embodiments, the Fc fragment includes the LALA mutations. LALA mutations are silencing mutations in an IgG Fc where the leucine (L) residues at position 234 and 235 (EU numbering) are mutated to alanine (A). The Fc fragment may be an IgG1, IgG2, IgG3 or IgG4 Fc fragment. In some embodiments, the Fc fragment further includes the N297A mutation at position 297 (EU numbering).

In some embodiment, the bispecific antibody has an anti-PD-1 portion, or more specifically, one, two, three, four or more anti-PD-1 VHH. In one example, an (or each) anti-PD-1 VHH is located at the N-terminal side of a VH of the anti-VEGF portion. In one example, an (or each) anti-PD-1 VHH is located at the N-terminal side of a VL of the anti-VEGF portion. In one example, an (or each) anti-PD-1 VHH is located at the C-terminal side of a VL of the anti-VEGF portion. In one example, an (or each) anti-PD-1 VHH is located at the C-terminal side of a Fc chain (of the anti-VEGF antibody).

In some embodiments, a single anti-PD-1 VHH is included in a peptide chain of the bispecific antibody. In some embodiments, exactly two anti-PD-1 VHH are included in a peptide chain of the bispecific antibody. In some embodiments, exactly three anti-PD-1 VHH are included in a peptide chain of the bispecific antibody.

In some embodiments, each heavy chain of the anti-VEGF antibody is fused to an anti-PD-1 VHH, such as at the N-terminus of the VH or the C-terminus of the Fc. In some embodiments, each heavy chain of the anti-VEGF antibody is fused to two anti-PD-1 VHH, such as both (concatenated) at the N-terminus of the VH or the C-terminus of the Fc. In some embodiments, each heavy chain of the anti-VEGF antibody is fused to a single anti-PD-1 VHH at the N-terminus of the VH or another anti-PD-1 VHH at the C-terminus of the Fc.

In some embodiments, the anti-PD-1 VHH is fused to the anti-VEGF portion through a peptide linker. An example linker is (G4S) 4 (SEQ ID NO:15). When two anti-PD-1 VHH are concatenated (e.g., B12D-6), they can be connected through a peptide. An example linker is (G4S)4 (SEQ ID NO:15).

Example anti-VEGF antibodies are described. In one embodiment, the anti-VEGF antibody includes the CDR regions of Bevacizumab (SEQ ID NO:9-14), which are shown in Table 1A. In some embodiments, the anti-VEGF portion includes a Fab fragment of Bevacizumab (VH (SEQ ID NO:3) and VL (SEQ ID NO:4) sequences are shown in FIG. 1).

Example anti-PD-1 single domain antibodies are also described. In one embodiment, the anti-PD-1 single domain antibody includes the three CDR regions of VH18 (SEQ ID NO: 5, 6 and 7). In one embodiment, the anti-PD-1 single domain antibody includes the three CDR regions of VH8M1 (SEQ ID NO:5, 6 and 8). In some embodiments, the anti-PD-1 single domain antibody includes the sequence of VH18 (SEQ ID NO:1). In some embodiments, the anti-PD-1 single domain antibody includes the sequence of VH8M1 (SEQ ID NO: 2).

Specific example heavy chain and light chain sequences are provided in Table 1B. In one embodiment, the bispecific antibody includes two heavy chains each having the amino acid sequence of SEQ ID NO:16 and two light chains each having the amino acid sequence of SEQ ID NO:17.

In one embodiment, the bispecific antibody includes two heavy chains each having the amino acid sequence of SEQ ID NO: 18 and two light chains each having the amino acid sequence of SEQ ID NO:17.

In one embodiment, the bispecific antibody includes two heavy chains each having the amino acid sequence of SEQ ID NO: 19 and two light chains each having the amino acid sequence of SEQ ID NO:17.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-expresses VEGF. In some embodiments, at least one of the cancer cells (e.g., stromal cells) in the patient over-expresses PD-1.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Cellular therapies, and more specifically chimeric antigen receptor (CAR) T-cell therapies, are also provided in the present disclosure. A suitable T cell can be used, that is put in contact with a bispecific antibody of the present disclosure (or alternatively engineered to express a bispecific antibody of the present disclosure). Upon such contact or engineering, the T cell can then be introduced to a cancer patient in need of a treatment. The cancer patient may have a cancer of any of the types as disclosed herein. The T cell can be, for instance, a tumor-infiltrating T lymphocyte, a CD4+ T cell, a CD8+ T cell, or the combination thereof, without limitation.

In some embodiments, the T cell was isolated from the cancer patient him- or her-self. In some embodiments, the T cell was provided by a donor or from a cell bank. When the T cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Anti-PD1/VEGF Bispecific Antibody

Each of two anti-PD1 nanobodies, VH18 and VH8M1, was fused to anti-VEGF antibody Bevacizumab to generate an anti-PD1-VEGF bispecific antibody.

The bispecific antibodies were of a full-length IgG-VHH fusion type. The anti-VEGF portion was the full IgG portion, while two anti-PD1 nanobodies were placed at the C-terminal side of IgG1 Fc fragment with LALA mutations, each via a (G4S) 4 linker (SEQ ID NO: 15).

Three bispecific antibodies were prepared, including B12D1-6, B12D1-9, and B12D1-10. Their structures are illustrated in FIG. 1. As shown in the figure, each of B12D1-9 and B12D1-10 contained a single copy of the anti-PD1 nanobody (sdAb) at the C-terminal end of each heavy chain. B12D1-6, by contrast, contained two concatenated anti-PD1 nanobodies. The linkers between the two nanobodies in B12D1-6 were also (G4S) 4 (SEQ ID NO: 15).

The antibody sequences are shown in Table 1.

TABLE 1

Antibody Sequences

| Name | Sequence | SEQ ID NO: |
|---|---|---|
| VH18 VHH | EVQLVESGGGLVQPGGSLRLSCAVSGNIYN RNFMGWFRQAPGKGREGVSAIYTGTSRTYY ADSVKGRFTISRDNAKNTVYLQMNSLRPED TAVYYCAADLRDGFWDTGVWNTWGQGTLVT VSS | 1 |
| VH8M1 VHH | EVQLVESGGGLVQPGGSLRLSCAVSGNIYN RNFMGWFRQAPGKGLEGVSAIYTGTSRTYY ADSVKGRFTISRDNSKNTVYLQMNSLRAED TAVYYCAADLREGFWDTGVWNTWGQGTLVT VSS | 2 |
| Bevacizumab VH | EVQLVESGGGLVQPGGSLRLSCAASGYTFT NYGMNWVRQAPGKGLEWVGWINTYTGEPTY AADFKRRFTFSLDTSKSTAYLQMNSLRAED TAVYYCAKYPHYYGSSHWYFDVWGQGTLVT VSS | 3 |
| Bevacizumab VL | DIQMTQSPSSLSASVGDRVTITCSASQDIS NYLNWYQQKPGKAPKVLIYFTSSLHSGVPS RFSGSGSGTDFTLTISSLQPEDFATYYCQQ YSTVPWTFGQGTKVEIK | 4 |

TABLE 1A

CDR Sequences

| Name | Sequence | SEQ ID NO: |
|---|---|---|
| VH18 VHH | RNFMG | 5 |
| | AIYTGTSRTYYADSVKG | 6 |
| | DLRDGFWDTGVWNT | 7 |
| VH8M1 VHH | RNFMG | 5 |
| | AIYTGTSRTYYADSVKG | 6 |
| | DLREGFWDTGVWNT | 8 |
| Bevacizumab VH | NYGMN | 9 |
| | WINTYTGEPTYAADFKR | 10 |
| | YPHYYGSSHWYFDV | 11 |
| Bevacizumab VL | SASQDISNYLN | 12 |
| | FTSSLHS | 13 |
| | QQYSTVPWT | 14 |

TABLE 1B

Bispecific Antibody Sequences

| Name | Sequence | SEQ ID NO: |
|---|---|---|
| B12D1-6 | Heavy Chain (VH-CH (Human IgG1LALA)-(G4S)4-VHH-(G4S)4-VHH) EVQLVESGGGLVQPGGSLRLSCAASGYTFT NYGMNWVRQAPGKGLEWVGWINTYTGEPTY AADFKRRFTFSLDTSKSTAYLQMNSLRAED TAVYYCAKYPHYYGSSHWYFDVWGQGTLVT VSSASTKGPSVFPLAPSSKSTSGGTAALGC LVKDYFPEPVTVSWNSGALTSGVHTFPAVL QSSGLYSLSSVVTVPSSSLGTQTYICNVNH | 16 |

TABLE 1B-continued

Bispecific Antibody Sequences

| Name | Sequence | SEQ ID NO: |
|---|---|---|
| | KPSNTKVDKKVEPKSCDKTHTCPPCPAPEA<br>AGGPSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGKGGGGSGGGGSGGGGSGGGGSEVQLVES<br>GGGLVQPGGSLRLSCAVSGNIYNRNFMGWF<br>RQAPGKGREGVSAIYTGTSRTYYADSVKGR<br>FTISRDNAKNTVYLQMNSLRPEDTAVYYCA<br>ADLRDGFWDTGVWNTWGQGTLVTVSSGGGG<br>SGGGGSGGGGSGGGGSEVQLVESGGGLVQP<br>GGSLRLSCAVSGNIYNRNFMGWFRQAPGKG<br>REGVSAIYTGTSRTYYADSVKGRFTISRDN<br>AKNTVYLQMNSLRPEDTAVYYCAADLRDGF<br>WDTGVWNTWGQGTLVTVSS | |
| | Light Chain VL-CL(Human Kappa)<br>DIQMTQSPSSLSASVGDRVTITCSASQDIS<br>NYLNWYQQKPGKAPKVLIYFTSSLHSGVPS<br>RFSGSGSGTDFTLTISSLQPEDFATYYCQQ<br>YSTVPWTFGQGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 17 |
| B12D1-9 | Heavy Chain (VH-CH (Human IgG1 L234A L235A)-(G4S)4-VHH)<br>EVQLVESGGGLVQPGGSLRLSCAASGYTFT<br>NYGMNWVRQAPGKGLEWVGWINTYTGEPTY<br>AADFKRRFTFSLDTSKSTAYLQMNSLRAED<br>TAVYYCAKYPHYYGSSHWYFDVWGQGTLVT<br>VSSASTKGPSVFPLAPSSKSTSGGTAALGC<br>LVKDYFPEPVTVSWNSGALTSGVHTFPAVL<br>QSSGLYSLSSVVTVPSSSLGTQTYICNVNH<br>KPSNTKVDKKVEPKSCDKTHTCPPCPAPEA<br>AGGPSVFLFPPKPKDTLMISRTPEVTCVVV<br>DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGGGGSGGGGSGGGGSGGGGSEVQLVESG<br>GGLVQPGGSLRLSCAVSGNIYNRNFMGWFR<br>QAPGKGREGVSAIYTGTSRTYYADSVKGRF<br>TISRDNAKNTVYLQMNSLRPEDTAVYYCAA<br>DLRDGFWDTGVWNTWGQGTLVTVSS | 18 |
| | Light Chain (VL-CL(Human Kappa))<br>DIQMTQSPSSLSASVGDRVTITCSASQDIS<br>NYLNWYQQKPGKAPKVLIYFTSSLHSGVPS<br>RFSGSGSGTDFTLTISSLQPEDFATYYCQQ<br>YSTVPWTFGQGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 17 |
| B12D1-10 | Heavy Chain (VH-CH (Human IgG1 L234A L235A)-(G4S)4-VHH)<br>EVQLVESGGGLVQPGGSLRLSCAASGYTFT<br>NYGMNWVRQAPGKGLEWVGWINTYTGEPTY<br>AADFKRRFTFSLDTSKSTAYLQMNSLRAED<br>TAVYYCAKYPHYYGSSHWYFDVWGQGTLVT<br>VSSASTKGPSVFPLAPSSKSTSGGTAALGC<br>LVKDYFPEPVTVSWNSGALTSGVHTFPAVL<br>QSSGLYSLSSVVTVPSSSLGTQTYICNVNH<br>KPSNTKVDKKVEPKSCDKTHTCPPCPAPEA<br>AGGPSVFLFPPKPKDTLMISRTPEVTCVVV | 19 |

TABLE 1B-continued

Bispecific Antibody Sequences

| Name | Sequence | SEQ ID NO: |
|---|---|---|
| | DVSHEDPEVKFNWYVDGVEVHNAKTKPREE<br>QYNSTYRVVSVLTVLHQDWLNGKEYKCKVS<br>NKALPAPIEKTISKAKGQPREPQVYTLPPS<br>RDELTKNQVSLTCLVKGFYPSDIAVEWESN<br>GQPENNYKTTPPVLDSDGSFFLYSKLTVDK<br>SRWQQGNVFSCSVMHEALHNHYTQKSLSLS<br>PGGGGGSGGGGSGGGGSGGGGSEVQLVESG<br>GGLVQPGGSLRLSCAVSGNIYNRNFMGWFR<br>QAPGKGLEGVSAIYTGTSRTYYADSVKGRF<br>TISRDNSKNTVYLQMNSLRAEDTAVYYCAA<br>DLREGFWDTGVWNTWGQGTLVTVSS | |
| | Light Chain (VL-CL(Human Kappa))<br>DIQMTQSPSSLSASVGDRVTITCSASQDIS<br>NYLNWYQQKPGKAPKVLIYFTSSLHSGVPS<br>RFSGSGSGTDFTLTISSLQPEDFATYYCQQ<br>YSTVPWTFGQGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 17 |

The resulting bispecific antibodies were produced transiently in CHO-K1 cells and applied to in vitro characterization including PD1 binding, VEGF binding and cell-based functional assays.

Example 2: Antigen Binding of the Anti-PD1-VEGF Bispecific Antibody

This example evaluated the antigen binding activity of the bispecific antibody of Example 1 to PD1 and VEGF.

ELISA Binding to VEGF

To test VEGF binding activity of the anti-PD1-VEGF bispecific antibodies, microtiter plates were coated with 100 μl human VEGF protein at 0.5 μg/ml diluted in PBS at 4° C. overnight, then blocked with 300 μl/well of 3% BSA. Three-fold dilution of antibodies starting from 100 nM were added to each well and incubated for 1 hours at 25° C. The plates were washed with ELISA washing buffer (1×DPBS with 0.5% Tween-20) and then incubated with peroxidase conjugated anti-human IgG secondary antibody for 60 minutes at 25° C. After washing, the plates were developed with TMB substrate and analyzed by microplate reader at OD450 nm. In this assay, anti-PD1-VEGF antibody VP101 developed by Akeso and Bevacizumab were included as reference antibodies.

Figure 2:
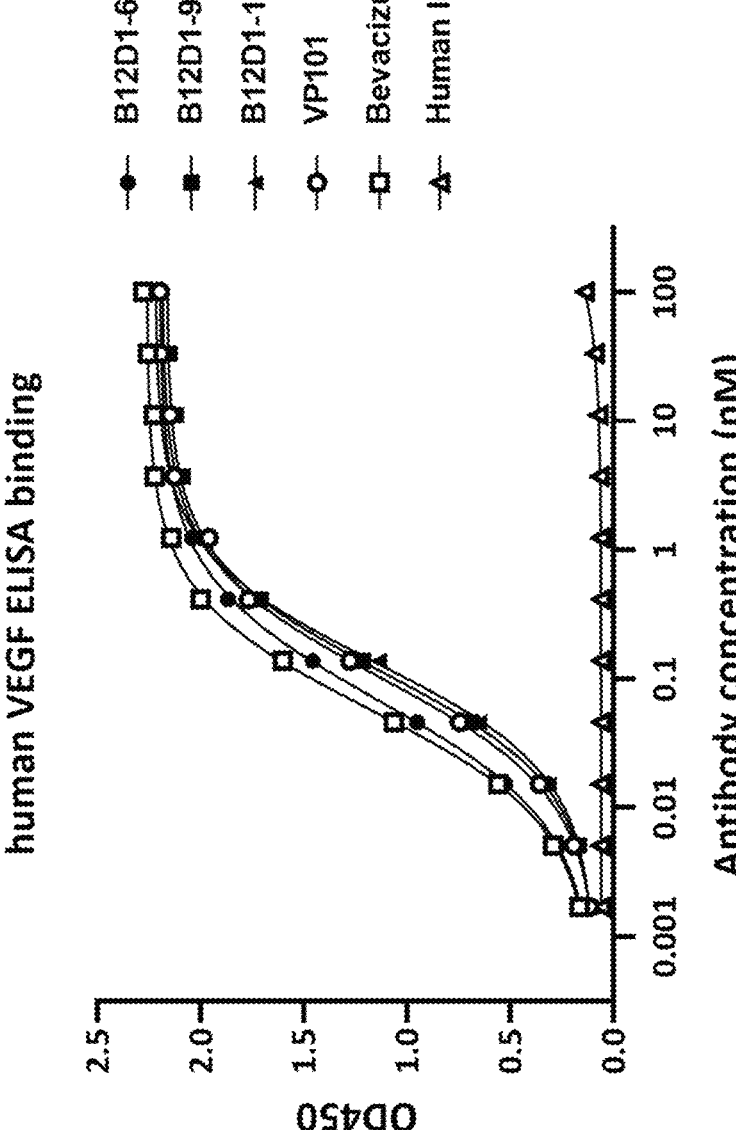
FIG. 2 shows that all the test anti-PD1-VEGF bispecific antibodies bound to human VEGF protein in a concentration-dependent manner.

As shown in FIG. 2 and Table 2, the anti-PD1-VEGF antibodies (B12D1-6, B12D1-9 and B12D1-10) efficiently bound to VEGF in a concentration-dependent manner. They showed comparable binding activity as the benchmark VP101 and the parental antibody Bevacizumab.

TABLE 2

| Human VEGF ELISA Binding | | |
|---|---|---|
| Antibody | EC50 (nM) | Top (OD450) |
| B12D1-6 | 0.068 | 2.198 |
| B12D1-9 | 0.114 | 2.163 |
| B12D1-10 | 0.134 | 2.219 |
| VP101 | 0.102 | 2.186 |
| Bevacizumab | 0.058 | 2.259 |

ELISA Binding to PD1

To evaluate PD1 binding activity of the test bispecific antibodies, human PD1 and cynomolgus PD1 diluted in PBS were coated on a microplate respectively at 4° C. overnight. Three-fold dilution of test antibodies starting from 100 nM were added to each well and incubated for 1 hours at 25° C. Then, the plates were washed with ELISA washing buffer (1×DPBS with 0.5% Tween-20) and incubated with peroxidase conjugated anti-human IgG secondary antibody for 60 minutes at 25° C. After washed four times with ELISA washing buffer, the plates were detected by TMB-ELISA substrate solution, then stopped by ELISA stopping solution and analyzed by microplate reader at OD450 nm. In this study, Pembrolizumab and anti-PD1 parental antibody VH18 were included as reference antibodies.

Figure 3:
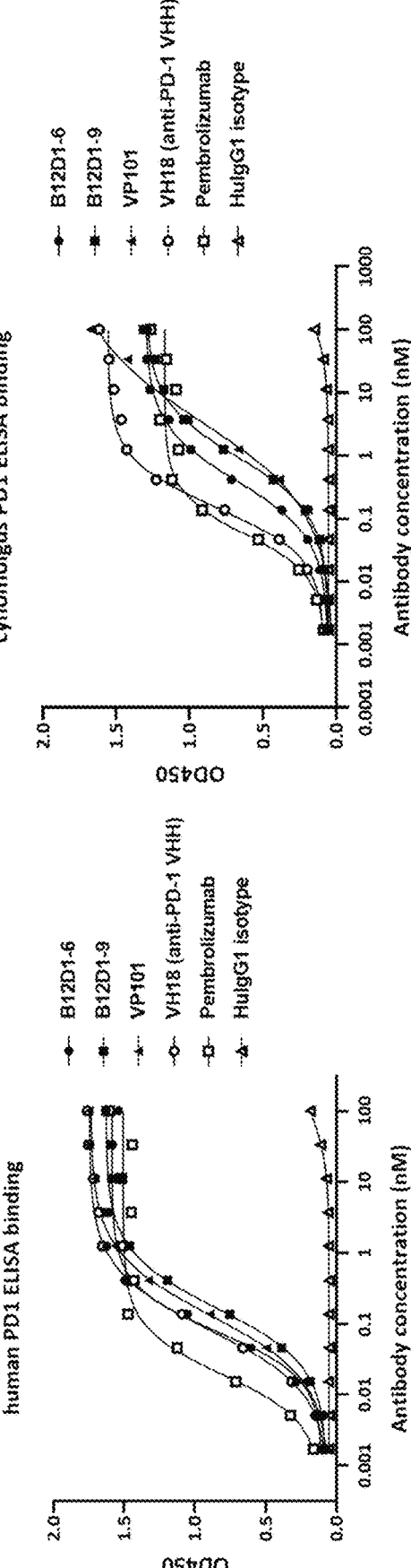
FIG. 3 shows that all the test anti-PD1-VEGF bispecific antibodies bound to human and cynomolgus PD1 protein in a concentration-dependent manner.

As shown in FIG. 3 and Table 3A-b, the anti-PD1-VEGF antibodies (B12D1-6 and B12D1-9) bound to human PD1 in a concentration-dependent manner with $EC_{50}$ of 0.078 nM for B12D1-6 and 0.169 nM for B12D1-9, comparable with the parental antibody and benchmark VP101. As for cynomolgus PD1 binding, B12D1-6 and B12D1-9 showed similar activity to VP101 but lower potency as compared to the parental antibody and Pembrolizumab.

TABLE 3A

| Human PD1 ELISA Binding | | |
|---|---|---|
| Antibody | EC50 (nM) | Top (OD450) |
| B12D1-6 | 0.078 | 1.587 |
| B12D1-9 | 0.169 | 1.629 |
| VP101 | 0.134 | 1.737 |
| VH18 (anti-PD-1 VHH) | 0.083 | 1.747 |
| Pembrolizumab | 0.019 | 1.507 |

TABLE 3B

| Cynomolgus PD1 ELISA Binding | | |
|---|---|---|
| Antibody | EC50 (nM) | Top (OD450) |
| B12D1-6 | 0.394 | 1.3 |
| B12D1-9 | 0.958 | 1.296 |
| VP101 | 3.491 | 1.831 |
| VH18 (anti-PD-1 VHH) | 0.151 | 1.556 |
| Pembrolizumab | 0.057 | 1.17 |

Cell-Based Binding to PD1

To further determine PD-1 binding activity of the bispecific antibodies, CHO-K1 cells overexpressing human PD-1 were incubated with different concentrations of anti-PD1-VEGF bispecific antibodies and reference antibodies at 4° C. for 30 minutes. Then, the cells were washed twice with FACS buffer and stained with PE conjugated secondary antibody at 4° C. for 30 minutes. After wash twice with FACS buffer, MFI of PE was analyzed by a NovoCyte flow cytometer. In this study, the benchmark VP101, Pembrolizumab and anti-PD-1 parental nanobodies were included as reference antibodies.

Figure 4:
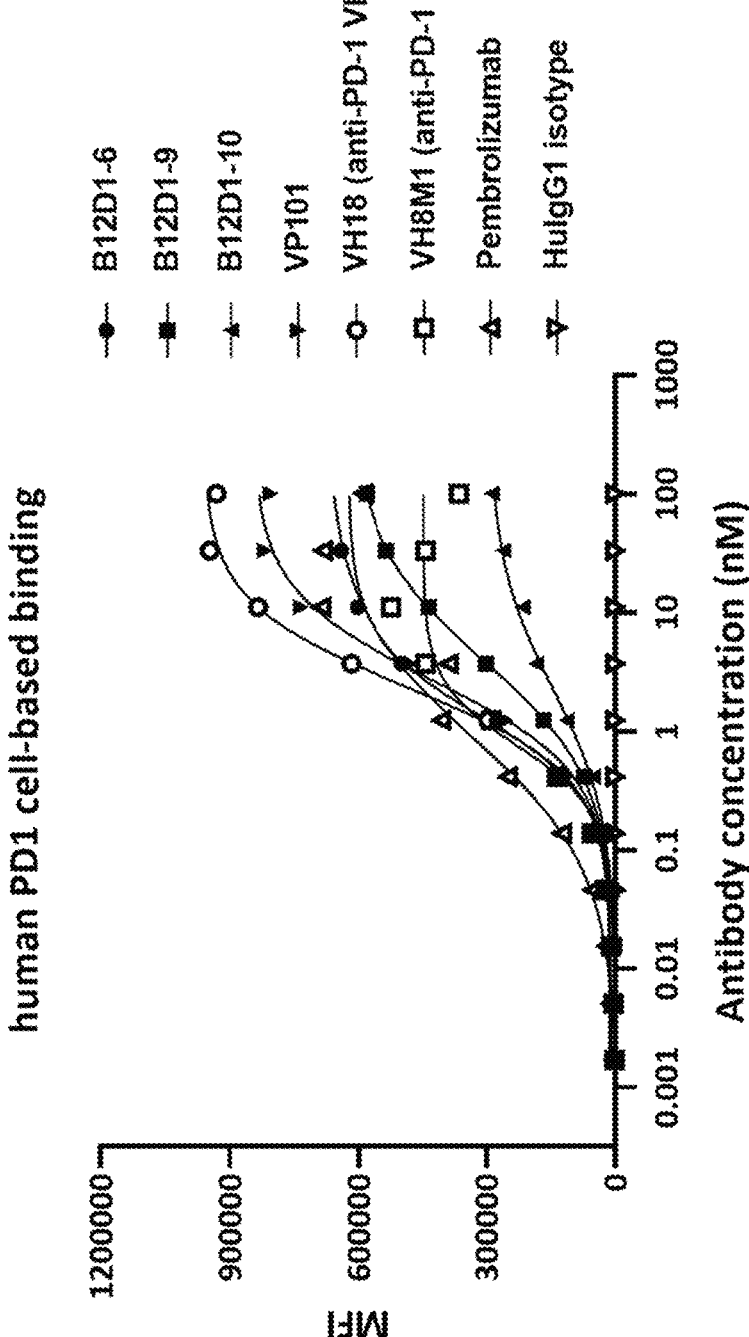
FIG. 4 shows that all the test anti-PD1-VEGF bispecific antibodies bound to human PD1 overexpressing CHO-K1 cells in a concentration-dependent manner.

As shown in FIG. 4 and Table 4, the anti-PD1-VEGF antibodies (B12D1-6, B12D1-9 and B12D1-10) bound to human PD-1 overexpressing CHO-K1 cells in a concentration-dependent manner. B12D1-6 showed similar binding $EC_{50}$ to that of Pembrolizumab.

TABLE 4

| Human PD1 Cell-Based Binding | | |
|---|---|---|
| Antibody | EC50 (nM) | Top (OD450) |
| B12D1-6 | 1.358 | 624586 |
| B12D1-9 | 3.947 | 616935 |
| B12D1-10 | 2.301 | 295903 |
| VP101 | 2.697 | 846203 |
| VH18 (anti-PD-1 VHH) | 2.352 | 962885 |
| VH8M1 (anti-PD-1 VHH) | 0.759 | 448131 |
| Pembrolizumab | 0.906 | 675641 |

Example 3: VEGF Neutralizing Activity in VEGF Reporter Assay

To evaluate the ability of anti-PD1-VEGF bispecific antibodies to neutralize soluble VEGF, a VEGF reporter gene assay was used.

In this assay, HEK293 cells were engineered to stably express VEGFR2 and have an NK-κB luciferase reporter construct integrated into the genome. Soluble VEGF at the concentration of 10 ng/ml was incubated with the HEK293 reporter cells in the presence of serial concentrations of the bispecific antibodies or reference antibodies for 6 hours at 37° C. Then, the substrate of luciferase was added, and the luminescence intensity was determined by a microplate reader.

Figure 5:
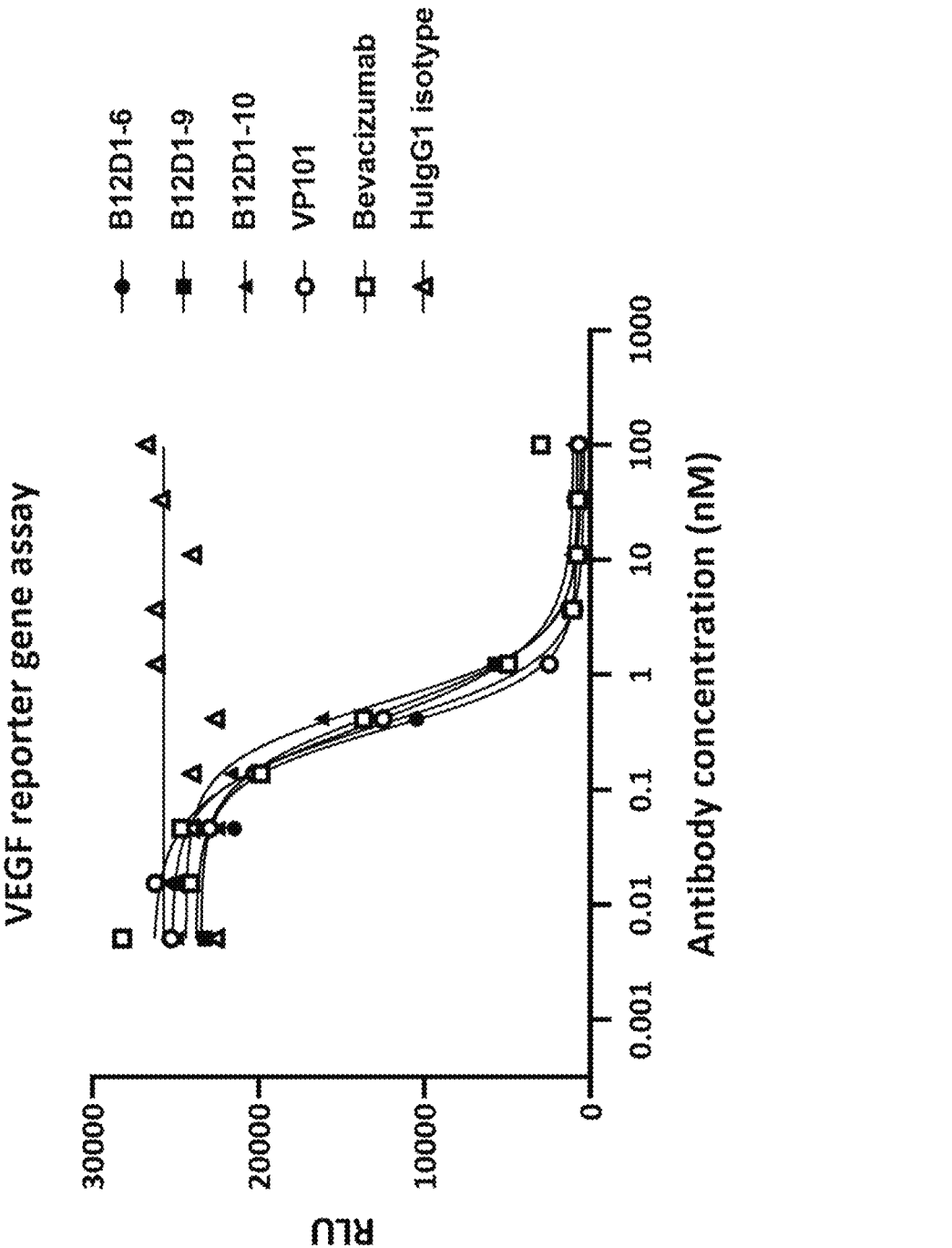
FIG. 5 shows that all the test anti-PD1-VEGF bispecific antibodies blocked VEGF-mediated signaling in a concentration-dependent manner in the VEGF reporter gene assay.

As shown in FIG. 5 and Table 5, the bispecific antibodies (B12D1-6, B12D1-9 and B12D1-10) efficiently blocked VEGF function in a concentration-dependent manner with $EC_{50}$ of 0.344 nM for B12D1-6, 0.493 nM for B12D1-9 and 0.567 nM for B12D1-10, comparable to those of the benchmark VP101 and anti-VEGF parental antibody Bevacizumab.

TABLE 5

| VEGF Reporter Gene Assay | | |
|---|---|---|
| Antibody | EC50 (nM) | Top (RLU) |
| B12D1-6 | 0.344 | 23469 |
| B12D1-9 | 0.493 | 23814 |
| B12D1-10 | 0.567 | 24392 |
| VP101 | 0.361 | 25225 |
| Bevacizumab | 0.358 | 26378 |

Example 4: PD1 Blocking Activity in PD1 Reporter Assay

To evaluate the effect of anti-PD1-VEGF bispecific antibodies in boosting T cell activation, this example used a robust in vitro functional PD-1 reporter gene assay.

In brief, human PD1 and a luciferase reporter gene under the control of NFAT-response element were simultaneously overexpressed on Jurkat T cells, while PDL1 and antigen-independent TCR stimulator OKT3 were over-expressed on CHO-K1 cells. When these two cell types were co-cultured, the negative signaling delivered on Jurkat cells by PD1-PDL1 ligation suppressed OKT3-mediated activation of TCR and NFAT-driven luciferase gene expression.

Figure 6:
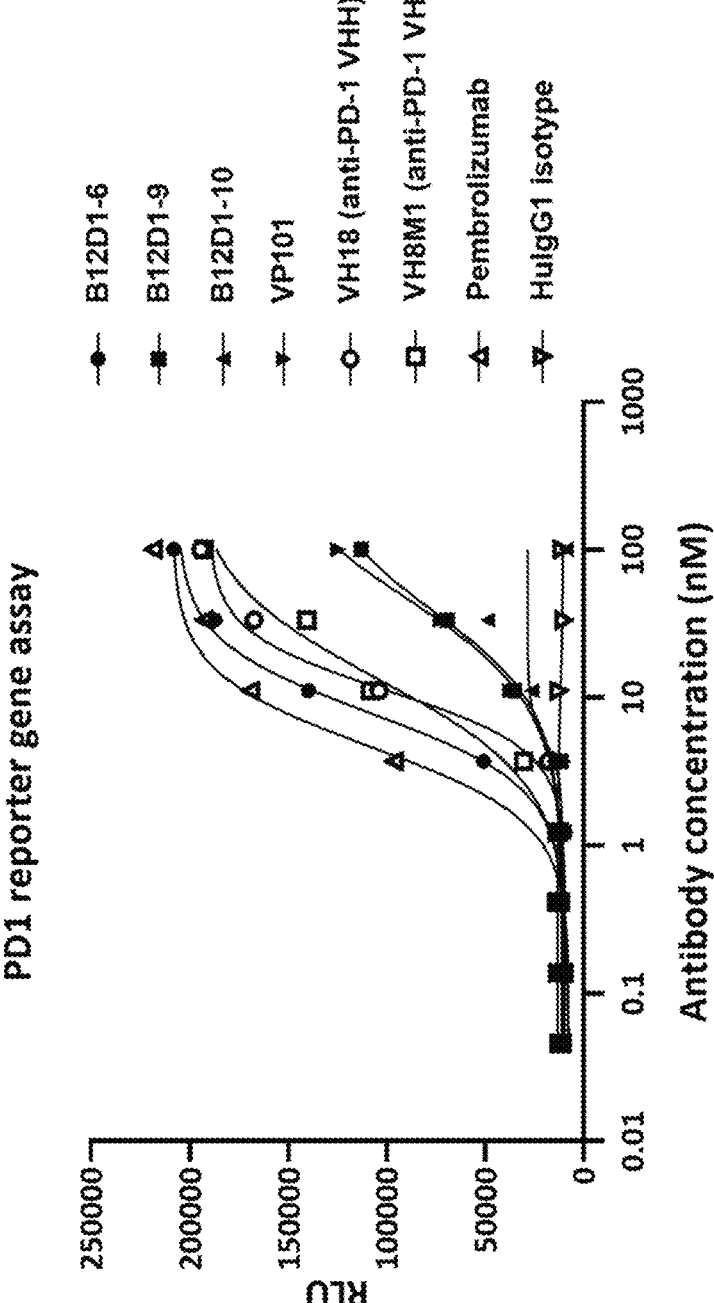
FIG. 6 shows that all the test anti-PD1-VEGF bispecific antibodies blocked PD1-mediated signaling in a concentration-dependent manner in the PD1 reporter gene assay.

As shown in FIG. 6 and Table 6, addition of serially diluted anti-PD1-VEGF bispecific antibodies efficiently enhanced luminescence signal by Jurkat-PD1 cells. The PD1 blockade activity of the antibody B12D1-6 was similar to that of the marketed antibody Pembrolizumab, and was superior to that of the benchmark VP101. B12D1-9 exhibited comparable activity to that of VP101.

TABLE 6

| PD1 blocking activity | | |
|---|---|---|
| Antibody | EC50 (nM) | Top (RLU) |
| B12D1-6 | 7.838 | 206610 |
| B12D1-9 | 37.93 | 140718 |
| B12D1-10 | 5.092 | 11044 |
| VP101 | 48.85 | 173443 |
| VH18 (anti-PD-1 VHH) | 11.17 | 190565 |
| VH8M1 (anti-PD-1 VHH) | 13.28 | 200748 |
| Pembrolizumab | 4.64 | 209010 |

Example 5: Stimulation of IFN-γ and IL-2 Release by Activated CD4+ T Cells in Mix Lymphocyte Reactions The effect of anti-PD1-VEGF bispecific antibodies on primary CD4+ T cells was further studied using PBMCs from healthy donors.

In brief, human dendritic cells (DC) were differentiated from CD14+ monocytes for 7 days. Purified CD4+ T cells isolated from another donor was co-cultured with DCs in the presence of serially diluted test antibodies for 5 days. The culture supernatant was collected on 2 days and 5 days, respectively. The concentration of IL-2 (2 days) and IFN-γ (5 days) in the supernatant was measured using a standard ELISA kit.

Figure 7A:
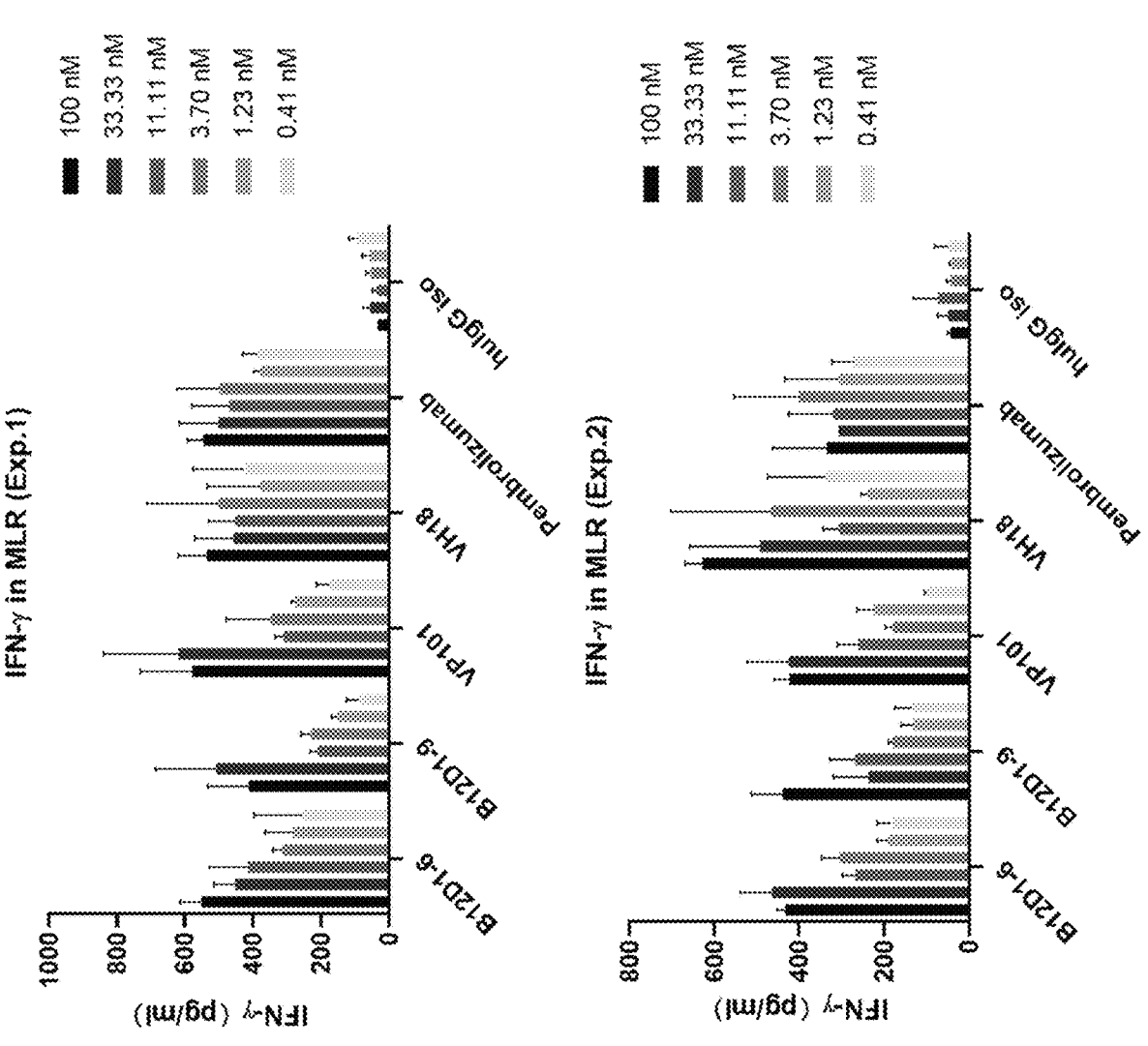
FIG. 7A-B show that the test anti-PD1-VEGF bispecific antibodies could stimulate IFN-$\gamma$ and IL-2 production in primary CD4+ T cells in the classical mixed lymphocyte reaction.
Figure 7B:

As shown in FIG. 7A-B, the anti-PD1-VEGF bispecific antibodies (B12D1-6 and B12D1-9) could stimulate IFN-γ and IL-2 production in primary CD4+ T cells in a concentration-dependent manner. Notably, the T cell activation potency of B12D1-6 was superior to that of VP101 and B12D1-9.

Example 6: Inhibition of VEGF-Induced Primary HUVEC Cells Proliferation

To evaluate the activity of anti-PD1-VEGF bispecific antibodies to inhibit VEGF-dependent proliferation of primary HUVEC cells, the HUVEC cells were incubated with different concentrations of the test antibody or reference antibodies in the presence of VEGF protein at 37° C. in 5% $CO_2$ incubator for 5 days. After incubation, the CellTiter-Glo was added to the mixture and then the luminescence intensity was determined by a microplate reader.

Figure 8:
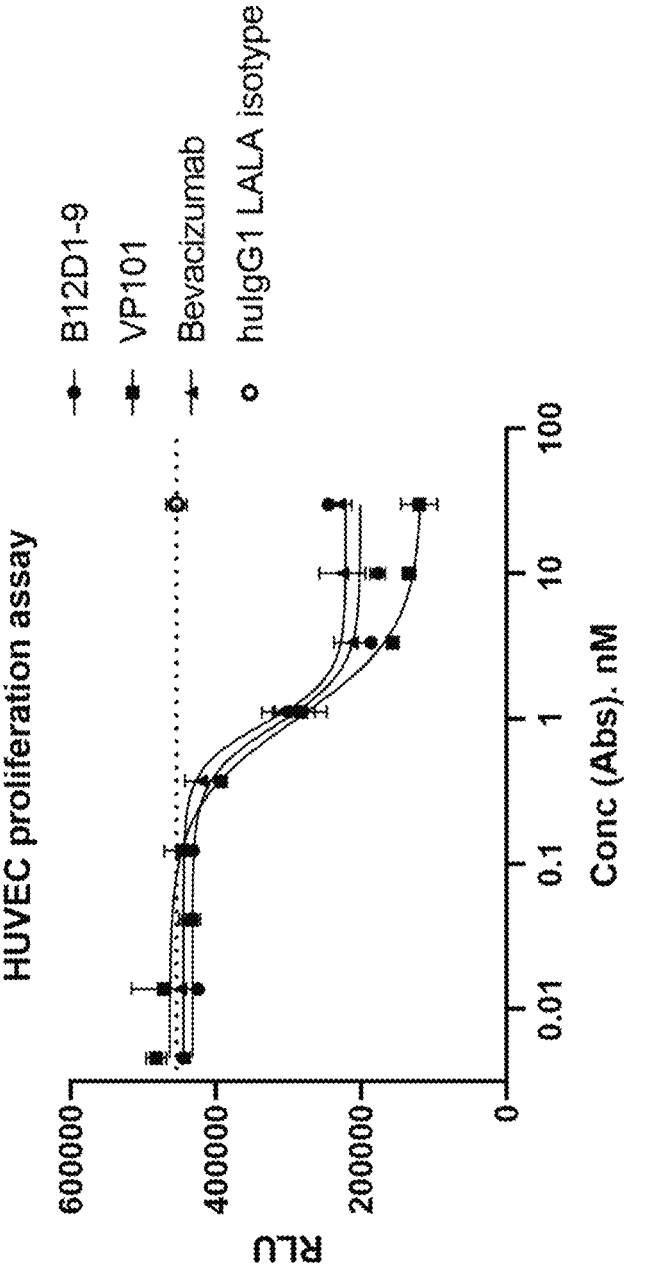
FIG. 8 shows that anti-PD-1-VEGF bi-specific antibody B12D1-9 inhibited VEGF-induced proliferation of HUVEC cells in a concentration-dependent manner.

As shown in FIG. 8, anti-PD-1-VEGF bi-specific antibody B12D1-9 inhibited VEGF-induced proliferation of HUVEC cells in a concentration-dependent manner. The $IC_{50}$ of B12D1-9 was estimated to be 0.907 nM (Table 7). The potency is comparable to those of the reference antibody VP101 and Bevacizumab.

TABLE 7

| Inhibition of VEGF-Induced Cell Proliferation | |
|---|---|
| Antibody | IC50 (nM) |
| B12D1-9 | 0.907 |
| VP101 | 0.985 |
| Bevacizumab | 0.932 |

Example 7: In Vivo Antitumor Efficacy of Anti-PD1-VEGF Bispecific Antibody in HuH-7 Humanized NOG Mouse Models To evaluate the anti-tumor efficacy of the anti-PD1-VEGF bispecific antibodies, a CDX tumor model using human PBMC-engrafted NOG mice inoculated with HuH-7 tumor cells was employed.

Figure 9:
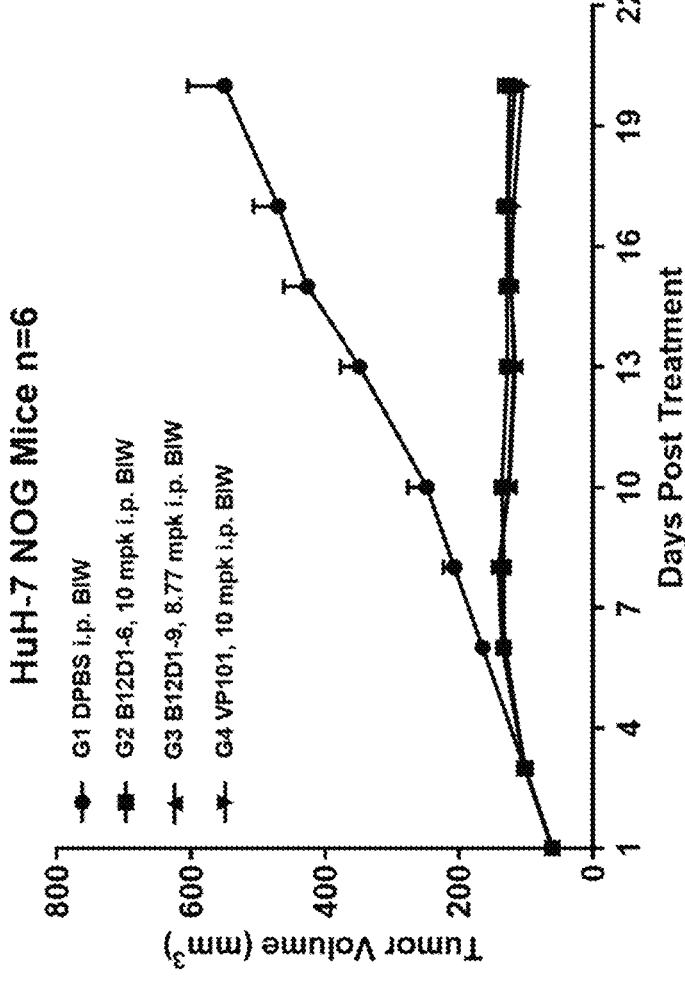
FIG. 9 shows that anti-PD-1-VEGF bi-specific antibody B12D1-6 and B12D1-9 exhibited strong anti-tumor efficacy in the HuH-7 xenograft model in PBMC humanized NOG mice.

Human PBMCs humanized NOG mice were subcutaneously implanted with $5 \times 10^6$ HuH-7 cells. When the average tumor volume grew to 60 mm³, tumor bearing mice were randomized into four groups (N=6/group) and were intraperitoneally administered vehicle (DPBS) or the test antibodies. The test antibodies B12D1-6, B12D1-9 and VP101 were given twice a week at 10 mg/kg, 8.77 mg/kg, and 10 mg/kg, respectively. Their dosages were equal under nmol/kg. Tumor volumes were monitored by caliper measurement three times per week for the duration of the experiment. As shown in FIG. 9, all the test antibodies had a significant antitumor efficacy on HuH-7 and the efficacy potency of B12D1-6 and B12D1-9 was comparable to the reference antibody VP101.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A bispecific antibody comprising an anti-VEGF portion and an anti-PD-1 portion, wherein the bispecific antibody comprises the amino acid sequences of SEQ ID NO: 17 and SEQ ID NO: 18.

2. A bispecific antibody comprising:
  i) a first polypeptide comprising the amino acid sequences of SEQ ID NO: 17;
  (ii) a second polypeptide comprising the amino acid sequence of SEQ ID NO: 18;
  (iii) a third polypeptide comprising the amino acid sequence of SEQ ID NO:18; and
  (iv) a fourth polypeptide comprising the amino acid sequence of SEQ ID NO:17.

3. The bispecific antibody of claim 2, wherein the first polypeptide and the second polypeptide are linked to each other via a disulfide bond, wherein the second polypeptide and the third polypeptide are linked to each other linked via two disulfide bonds, and wherein the third polypeptide and the fourth polypeptide are linked to each other linked via a disulfide bond.

4. A composition comprising the bispecific antibody of claim 1 and a pharmaceutically acceptable carrier.

5. A polynucleotide encoding (i) the amino acid sequence of SEQ ID NO: 18 or (ii) the amino acid sequences of SEQ ID NO: 17 and SEQ ID NO: 18.

6. A cell comprising (i) one or more polynucleotides encoding the amino acid sequences of SEQ ID NO: 17 and SEQ ID NO: 18 or (ii) one or more polynucleotides encoding the amino acid sequence of SEQ ID NO: 17 and one or more polynucleotides encoding the amino acid sequence of SEQ ID NO: 18.

7. A method of treating cancer in a patient in need thereof, comprising administering to the patient an effective amount of the bispecific antibody of claim 1.

8. The method of claim 7, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

9. The method of claim 7, wherein the cancer is bladder cancer.

10. The method of claim 7, wherein the cancer is breast cancer.

11. The method of claim 7, wherein the cancer is colorectal cancer.

12. The method of claim 7, wherein the cancer is head and neck cancer.

13. The method of claim 7, wherein the cancer is kidney cancer.

14. The method of claim 7, wherein the cancer is lung cancer.

15. The method of claim 7, wherein the cancer is melanoma.

16. The cell of claim 6, wherein the cell is a CHO-K1 cell.

17. A method of making the bispecific antibody of claim 1, comprising (i) expressing one or more polynucleotides encoding the amino acid sequences of SEQ ID NO:17 and SEQ ID NO:18 in a CHO cell; or (ii) expressing one or more polynucleotides encoding the amino acid sequence of SEQ ID NO: 17 and one or more polynucleotides encoding the amino acid sequence of SEQ ID NO:18 in a CHO cell.

18. A bispecific antibody made by the method of claim 17.

19. The bispecific antibody of claim 1, wherein the bispecific antibody is produced in a CHO-K1 cell.

20. The bispecific antibody of claim 1, wherein the bispecific antibody is produced by (i) expressing one or more polynucleotides encoding the amino acid sequences of SEQ ID NO: 17 and SEQ ID NO:18 in a CHO-K1 cell, or (ii) expressing one or more polynucleotides encoding the amino acid sequence of SEQ ID NO: 17 and one or more polynucleotides encoding the amino acid sequence of SEQ ID NO:18 in a CHO-K1 cell.

21. A bispecific antibody comprising an anti-VEGF portion and an anti-PD-1 portion, wherein the bispecific antibody comprises the amino acid sequences of SEQ ID NO: 17 and SEQ ID NO:16.

22. A bispecific antibody comprising:
  (i) a first polypeptide comprising the amino acid sequence of SEQ ID NO:17;
  (ii) a second polypeptide comprising the amino acid sequence of SEQ ID NO:16;
  (iii) a third polypeptide comprising the amino acid sequence of SEQ ID NO:16; and
  (iv) a fourth polypeptide comprising the amino acid sequence of SEQ ID NO:17.

23. The bispecific antibody of claim 22, wherein the first polypeptide and the second polypeptide are linked to each other via a disulfide bond, wherein the second polypeptide and the third polypeptide are linked to each other linked via two disulfide bonds, and wherein the third polypeptide and the fourth polypeptide are linked to each other linked via a disulfide bond.

24. A composition comprising the bispecific antibody of claim 21 and a pharmaceutically acceptable carrier.

25. A polynucleotide encoding (i) the amino acid sequence of SEQ ID NO:16 or (ii) the amino acid sequences of SEQ ID NO 17 and SEQ ID NO:16.

26. A cell comprising (i) one or more polynucleotides encoding the amino acid sequences of SEQ ID NO:17 and SEQ ID NO:16 or (ii) one or more polynucleotides encoding the amino acid sequence of SEQ ID NO: 17 and one or more polynucleotides encoding the amino acid sequence of SEQ ID NO:16.

27. The cell of claim 26, wherein the cell is a CHO-K1 cell.

28. A method of making the bispecific antibody of claim 21, comprising (i) expressing one or more polynucleotides encoding the amino acid sequences of SEQ ID NO: 17 and SEQ ID NO:16 in a CHO cell or (ii) expressing one or more polynucleotides encoding the amino acid sequence of SEQ ID NO: 17 and one or more polynucleotides encoding the amino acid sequence SEQ ID NO:16 in a CHO cell.

29. A bispecific antibody made by the method of claim 28.

30. The bispecific antibody of claim 21, wherein the bispecific antibody is produced in a CHO-K1 cell.

31. The bispecific antibody of claim 21, wherein the bispecific antibody is produced by (i) expressing one or more polynucleotides encoding the amino acid sequences of SEQ ID NO: 17 and SEQ ID NO:16 in a CHO-K1 cell; or (ii) expressing one or more polynucleotides encoding the amino acid sequence of SEQ ID NO:17 and one or more polynucleotides encoding the amino acid sequence of SEQ ID NO: 16 in a CHO-K1 cell.

32. A method of treating cancer in a patient in need thereof, comprising administering to the patient an effective amount of the bispecific antibody of claim 21.

33. The method of claim 32, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

34. The method of claim 32, wherein the cancer is bladder cancer.

35. The method of claim 32, wherein the cancer is breast cancer.

36. The method of claim 32, wherein the cancer is colorectal cancer.

37. The method of claim 32, wherein the cancer is head and neck cancer.

38. The method of claim 32, wherein the cancer is kidney cancer.

39. The method of claim 32, wherein the cancer is lung cancer.

40. The method of claim 32, wherein the cancer is melanoma.

41. A bispecific antibody comprising an anti-VEGF portion and an anti-PD-1 portion, wherein the bispecific antibody comprises the amino acid sequences of SEQ ID NO: 17 and SEQ ID NO:19.

42. A bispecific antibody comprising:
(i) a first polypeptide comprising the amino acid sequence of SEQ ID NO:17;
(ii) a second polypeptide comprising the amino acid sequence of SEQ ID NO:19;

(iii) a third polypeptide comprising the amino acid sequence of SEQ ID NO:19; and
(iv) a fourth polypeptide comprising the amino acid sequence of SEQ ID NO:17.

43. The bispecific antibody of claim 42, wherein the first polypeptide and the second polypeptide are linked to each other via a disulfide bond, wherein the second polypeptide and the third polypeptide are linked to each other linked via two disulfide bonds, and wherein the third polypeptide and the fourth polypeptide are linked to each other linked via a disulfide bond.

44. A composition comprising the bispecific antibody of claim 41 and a pharmaceutically acceptable carrier.

45. A polynucleotide encoding (i) the amino acid sequence of SEQ ID NO:19 or (ii) the amino acid sequences of SEQ ID NO:17 and SEQ ID NO:19.

46. A cell comprising (i) one or more polynucleotides encoding the amino acid sequences of SEQ ID NO:17 and SEQ ID NO:19 or (ii) one or more polynucleotides encoding the amino acid sequence of SEQ ID NO: 17 and one or more polynucleotides encoding the amino acid sequence of SEQ ID NO: 19.

47. The cell of claim 46, wherein the cell is a CHO-K1 cell.

48. A method of making the bispecific antibody of claim 41, comprising (i) expressing one or more polynucleotides encoding the amino acid sequences of SEQ ID NO: 17 and SEQ ID NO:19 in a CHO cell; or (ii) expressing one or more polynucleotides encoding the amino acid sequence of SEQ ID NO:17 and one or more polynucleotides encoding the amino acid sequence SEQ ID NO:19 in a CHO cell.

49. A bispecific antibody made by the method of claim 48.

50. The bispecific antibody of claim 41, wherein the bispecific antibody is produced in a CHO-K1 cell.

51. The bispecific antibody of claim 41, wherein the bispecific antibody is produced by (i) expressing one or more polynucleotides encoding the amino acid sequences of SEQ ID NO: 17 and SEQ ID NO:19 in a CHO-K1 cell; or (ii) expressing one or more polynucleotides encoding the amino acid sequence of SEQ ID NO: 17 and one or more polynucleotides encoding the amino acid sequence of SEQ ID NO: 19 in a CHO-K1 cell.

52. A method of treating cancer in a patient in need thereof, comprising administering to the patient an effective amount of the bispecific antibody of claim 41.

53. The method of claim 52, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

54. The method of claim 52, wherein the cancer is bladder cancer.

55. The method of claim 52, wherein the cancer is breast cancer.

56. The method of claim 52, wherein the cancer is colorectal cancer.

57. The method of claim 52, wherein the cancer is head and neck cancer.

58. The method of claim 52, wherein the cancer is kidney cancer.

59. The method of claim 52, wherein the cancer is lung cancer.

60. The method of claim 52, wherein the cancer is melanoma.

* * * * *